(12) United States Patent
Mattson et al.

(10) Patent No.: US 9,357,973 B2
(45) Date of Patent: Jun. 7, 2016

(54) X-RAY BEAM TRANSMISSION PROFILE SHAPER

(75) Inventors: Rodney Arnold Mattson, Mentor, OH (US); Randall Peter Luhta, Chardon, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 118 days.

(21) Appl. No.: 14/125,337

(22) PCT Filed: Jun. 5, 2012

(86) PCT No.: PCT/IB2012/052814
§ 371 (c)(1),
(2), (4) Date: Dec. 11, 2013

(87) PCT Pub. No.: WO2013/001386
PCT Pub. Date: Jan. 3, 2013

(65) Prior Publication Data
US 2014/0112431 A1   Apr. 24, 2014

Related U.S. Application Data

(60) Provisional application No. 61/503,141, filed on Jun. 30, 2011.

(51) Int. Cl.
*A61B 6/00* (2006.01)
*G21K 1/10* (2006.01)
*A61B 6/03* (2006.01)
*G21K 1/02* (2006.01)
*A61B 6/06* (2006.01)

(52) U.S. Cl.
CPC .............. *A61B 6/4035* (2013.01); *A61B 6/035* (2013.01); *G21K 1/02* (2013.01); *G21K 1/10* (2013.01); *A61B 6/06* (2013.01)

(58) Field of Classification Search
CPC ........... G21K 1/04; G21K 1/046; G21K 1/10; G21K 5/04; A61B 6/06; A61B 6/4035; A61B 6/405
See application file for complete search history.

(56) References Cited

U.S. PATENT DOCUMENTS

| 2,216,326 | A | * | 10/1940 | Smith | ................ G21K 1/10 378/158 |
|---|---|---|---|---|---|
| 3,717,768 | A | | 2/1973 | Edholm et al. | |
| 3,755,672 | A | | 8/1973 | Edholm et al. | |
| 4,277,684 | A | * | 7/1981 | Carson | ............................ 378/7 |
| 4,672,648 | A | | 6/1987 | Mattson et al. | |
| 5,493,599 | A | | 2/1996 | Mattson | |
| 6,127,688 | A | * | 10/2000 | Wu | .................... G21K 1/10 250/492.3 |
| 2002/0118791 | A1 | * | 8/2002 | Snoeren et al. | ............... 378/158 |
| 2003/0198319 | A1 | | 10/2003 | Toth et al. | |
| 2010/0061511 | A1 | | 3/2010 | Heid | |
| 2010/0074393 | A1 | * | 3/2010 | Thran et al. | ....................... 378/4 |
| 2014/0112431 | A1 | * | 4/2014 | Mattson et al. | ................. 378/16 |
| 2015/0302946 | A1 | * | 10/2015 | Ofer | ........................ A61B 6/06 378/160 |

FOREIGN PATENT DOCUMENTS

WO   02052580   A1   7/2002

* cited by examiner

*Primary Examiner* — Thomas R Artman

(57) ABSTRACT

An imaging system (300) includes a radiation source (308) that emits radiation from a focal spot (312) in a direction of an examination region. The imaging system further includes a beam shaper (314), located between the focal spot and the examination region, that shapes an x-ray transmission profile of the radiation emitted from the source and incident on the beam shaper such that the radiation leaving the beam shaper has a pre-determined transmission profile.

21 Claims, 8 Drawing Sheets

X-RAY BEAM TRANSMISSION PROFILE SHAPER

CROSS REFERENCE TO RELATED APPLICATIONS

This application is a national filing of PCT application Serial No. PCT/IB2012/052814, filed Jun. 5, 2012, published as WO 2013/001386 A1 on Jan. 3, 2013, which claims the benefit of U.S. provisional application Ser. No. 61/503,141 filed Jun. 30, 2011, which is incorporated herein by reference.

FIELD OF THE INVENTION

The following generally relates to shaping an x-ray beam transmission profile and is described with particular application to computed tomography (CT); however, the following is also amenable to other imaging modalities such as x-ray.

BACKGROUND OF THE INVENTION

A typical CT scanner includes an x-ray tube that emits radiation from a focal spot in a direction of an examination region. A source collimator is disposed between the focal spot and the examination region and collimates the emitted radiation to produce a beam having a pre-determined geometrical shape (e.g., fan, cone, wedge, etc.). The collimated beam traverses the examination region and a portion of an object or subject therein (which attenuates the beam as a function of the radiodensity of the object or subject) and illuminates a detector array disposed across the examination region, opposite the x-ray tube. The detector produces projection data indicative of the detected radiation. The projection data can be reconstructed to generate volumetric image data indicative of the portion of the object or subject.

A pre-patient radiation filter (often referred to as a bow-tie filter due to its shape) has been positioned between the focal spot and the collimator to spatially attenuate the emitted radiation to shape the transmission profile. FIG. 1 schematically illustrates an example of a bow-tie filter 102 in connection with a focal spot 104, a source collimator 106, an x-ray beam 108, a detector array 110, an examination region 112, and a portion of a subject or object 114 therein. Due to its shape, the bow-tie filter 102 heavily filters regions of the beam 108 that traverse only air, lightly filters the region of the beam 108 that traverses the subject 114, and varies the degree of filtering for the transitions there between. FIG. 2 illustrates an example resulting transmission profile 200 as a function of beam angle, where a y-axis 202 represents transmission and an x-axis 204 represents beam angle. Note that the profile 200 varies as a function of the thickness of filter 102.

Unfortunately, the bow-tie filter 102 also preferentially filters lower energy rays relative to higher energy rays, thereby changing the x-ray spectrum of the beam exiting the filter 102, relative to the beam entering the filter 102. As such, the spectrum of the beam used to scan a subject or object may not be the optimal or desired spectrum. Furthermore, x-rays that are scattered by the bow-tie filter 102 degrade image quality and may require image processing scatter corrections to mitigate. Scatter from the bow-tie filter 102 may also contribute to patient dose while not contributing to diagnostic information in the reconstructed images. Furthermore, a geometry of the bow-tie filter 102 defines a minimum spacing between the focal spot 104 and the collimator 106, which may limit the size of the examination region 112 for a given focal spot location and/or require moving the x-ray tube for a given examination region size.

In view of at least the above, there is an unresolved need for other approaches for shaping the transmission profile of the radiation beam of a CT scanner.

SUMMARY OF THE INVENTION

Aspects of the present application address the above-referenced matters and others.

According to one aspect, an imaging system includes a radiation source that emits radiation from a focal spot in a direction of an examination region. The imaging system further includes a beam shaper, located between the focal spot and the examination region, that shapes an x-ray transmission profile of the radiation emitted from the source and incident on the beam shaper such that the radiation leaving the beam shaper has a pre-determined transmission profile.

In another aspect, a method shaping a transmission profile of an x-ray beam used to scan a subject or object so that the transmission profile decreases from a central region of the beam to a periphery of the beam using a beam shaper that includes a two dimensional array of individual attenuators which are separated from each other and which are arranged such that a lesser density of the attenuators are located nearer the central region and greater density of the attenuators are located farther from the central region, and scanning the subject or object using the beam with the shaped transmission profile.

In another aspect, a beam shaper configured for use in an imaging system includes a two dimensional array of individual radiation attenuating elements, separated from each other and arranged with respect to each other such that a density of the attenuating elements varies along an x-axis direction, wherein the individual radiation attenuating elements fully or substantially fully attenuate x-rays.

Still further aspects of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 3:
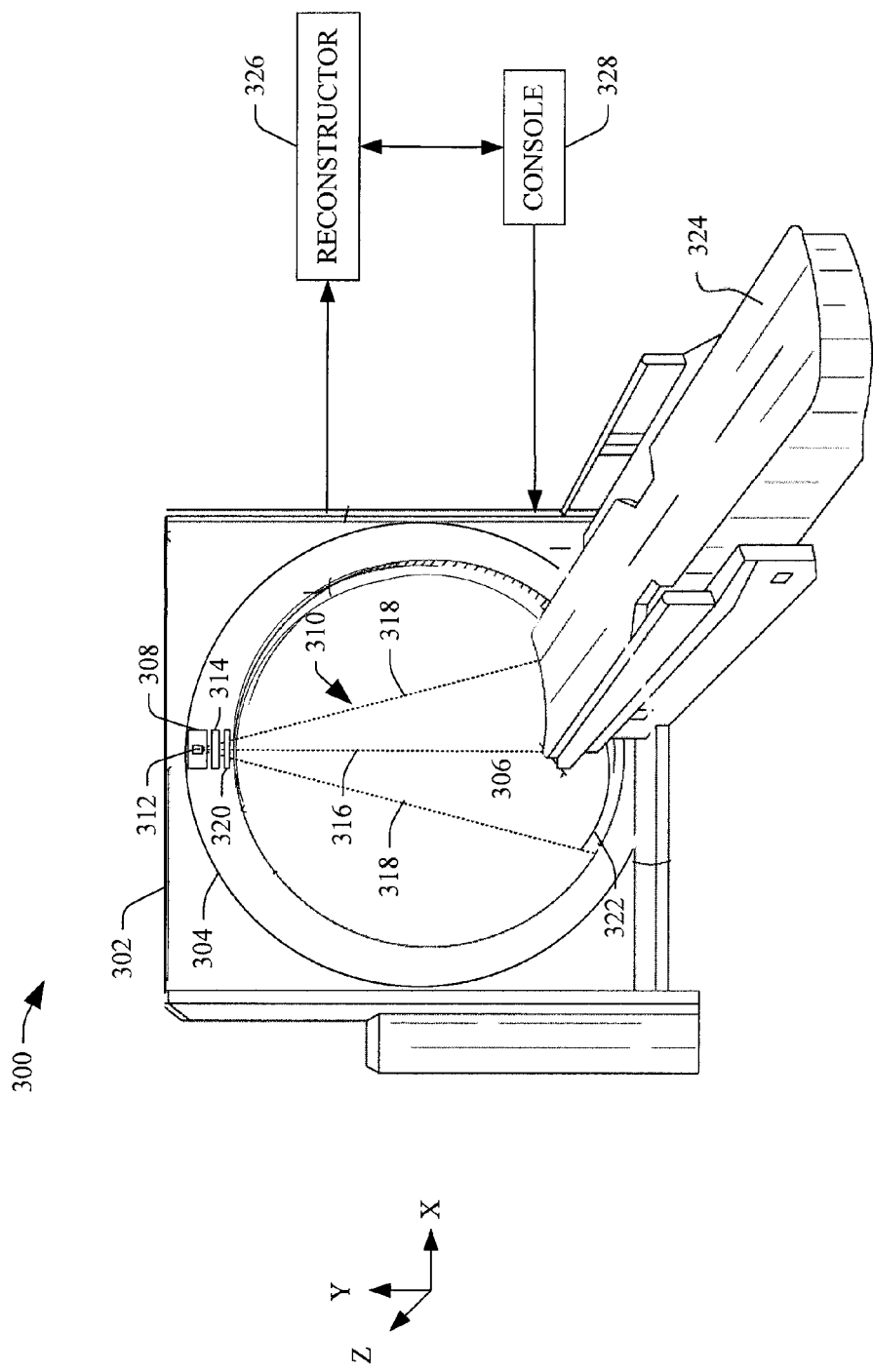
FIG. 3 schematically illustrates an example imaging system including a beam shaper that shapes a transmission profile of radiation emitted by the imaging system.

FIG. 3 illustrates an imaging system 300 such as a computed tomography (CT) scanner. The imaging system 300 includes a stationary gantry 302 and a rotating gantry 304, which is rotatably supported by the stationary gantry 302. The rotating gantry 304 rotates around an examination region 306 about a longitudinal or z-axis.

A radiation source 308, such as an x-ray tube, is supported by the rotating gantry 304 and rotates with the rotating gantry 304 about the examination region 306. The radiation source 308 emits radiation 310 from a focal spot 312 of an anode (not visible) of the source 308 essentially in all directions, including a direction of the examination region 306.

Figure 1:
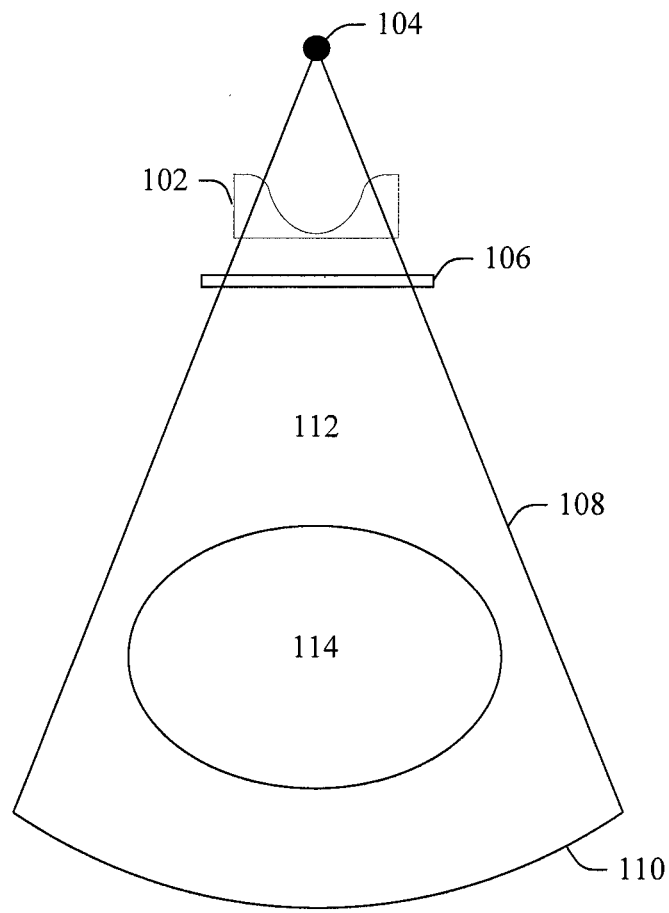
FIG. 1 schematically illustrates a prior approach to shaping a transmission profile of a radiation beam for a CT scanner.
Figure 2:
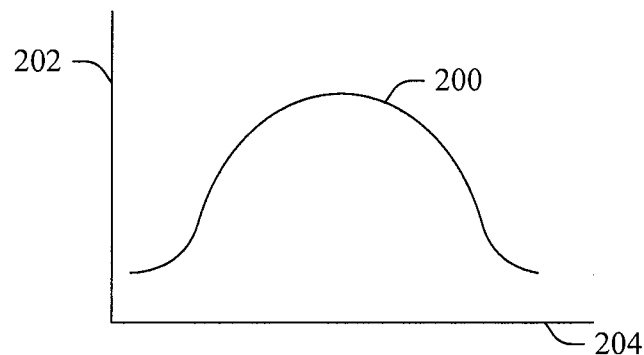
FIG. 2 illustrates an example shaped transmission profile using the prior art approach of FIG. 1.

A beam shaper 314 is arranged between the focal spot 312 and the examination region 306. The illustrated beam shaper 314 is configured to shape a transmission profile of the beam 310. As described in greater detail below, the beam shaper 314 shapes the transmission profile of the emitted radiation so that transmission is greater nearer a central ray 316 of the beam 310 and decreases in a direction away from the ray 316 and towards outer rays 318. As such, the beam shaper 314 can be used in place of or in combination with a conventional bow-tie filter such as the bow-tie filter depicted in FIG. 2. The transmission can be varied (linearly or non-linearly, in a deterministic or locally random but overall defined manner) in a single dimension, for example, along the x-direction, or in multiple dimensions, for example, in the x-z plane.

Furthermore, the beam shaper 314 can be located with respect to the focal spot 312 such that it substantially filters off-focal rays, which may reduce patient dose and mitigate need for off-focal image processing corrections. In addition, the beam shaper 314 can be thin and cause little to no scatter, which may reduce patient dose from scatter and mitigate need for scatter image processing corrections. Further, the beam shaper 314 has little to no effect on the x-ray spectrum so that the x-ray spectrum of the radiation leaving the beam shaper 314 is approximately the same as the x-ray spectrum of the radiation incident thereon. Moreover, the footprint of the beam shaper 314 is relatively smaller in the y-axis direction, allowing for larger examination regions 306 for a given focal spot 312 location, relative to a configuration using a bow-tie filter.

A source collimator 320 collimates the beam 310 to a pre-determined geometrical shape of interest, including a fan, a cone, a wedge, or other shaped beam 310 that traverses the examination region 306.

A radiation sensitive detector array 322 is located opposite the radiation source 308, across the examination region 306. The detector array 322 includes a two dimensional (2D) array of detector pixels that detect radiation traversing the examination region 306 and generate projection data indicative thereof.

A support 324, such as a couch, supports a subject in the examination region 306 and can be used to position the subject with respect to x, y, and/or z axes before, during and/or after scanning.

A reconstructor 326 reconstructs the projection data and generates three dimensional (3D) volumetric image data indicative of the examination region 306 and an object or subject therein. The resulting volumetric image data can be processed by an image processor or the like to generate one or more images.

A general purpose computing system serves as an operator console 328, and includes an output device such as a display and an input device such as a keyboard, mouse, and/or the like. Software resident on the console 328 allows the operator to control the operation of the system 300, for example, allowing the operator to initiate scanning, etc.

Figure 4:
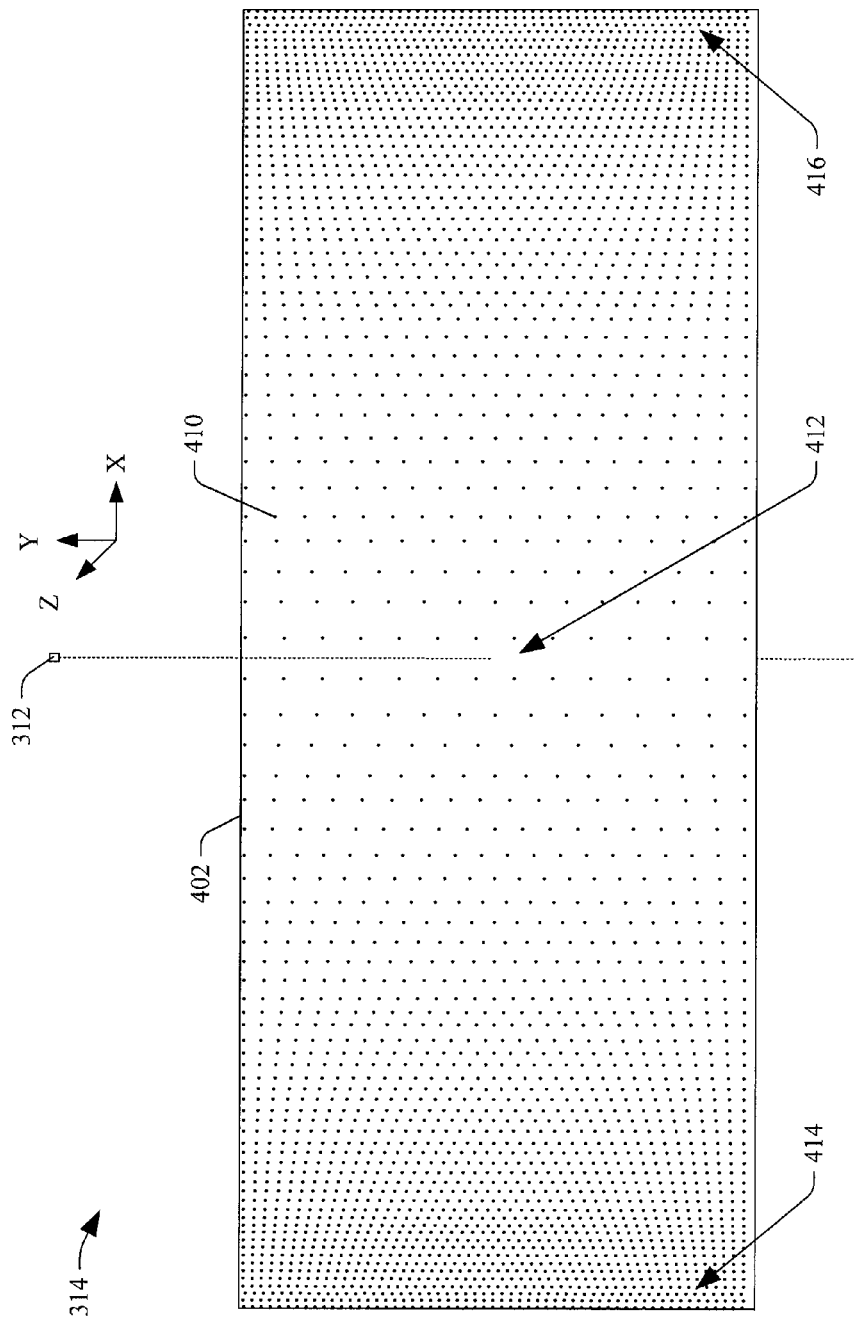
FIG. 4 schematically illustrates an example beam shaper that includes a plurality of radiation attenuating elements separated by radiation transparent regions.

FIG. 4 schematically illustrates a non-limiting example of the beam shaper 314, looking into the beam shaper 314 in a direction from the focal spot to the examination region along the y direction.

In this example, the beam shaper 314 includes a support or substrate 402. The substrate 402 includes a low Z material such as aluminum, plastic, etc. As such, the substrate 402 is substantially transparent to x-ray radiation in that x-rays traverse the substrate 402 with little to no attenuation. As a result, the x-ray spectrum of the beam leaving the beam shaper 314 is approximately the same as the x-ray spectrum of the beam incident on the beam shaper 314. In one instance, this makes the beam shaper 314 well suited for spectral or multi-energy applications.

The illustrated substrate 402 is rectangular shaped with a geometry of less than six inches (but greater than zero) in length by less than three inches (but greater than zero) in width. The absorber material can have a thickness in a range from a quarter of a millimeter to 10 millimeters. In one instance, the thickness is such that the beam shaper 314 can fit into the beam port of the x-ray tube, which is located between the focal spot 312 and the collimator 320 and proximate to the focal spot 312, of a conventional CT scanner x-ray tube, and thus not require additional space. In other embodiments, the substrate 402 is otherwise shaped (e.g., square, circular, elliptical, octagon, etc.) and/or the length, width and/or thickness respectively can be greater than six inches, six inches, and a half a millimeter. In the illustrated embodiment, the thickness of the substrate 402 is generally uniform across the substrate 402. In other embodiments, the thickness can be non-uniform.

Figure 12:
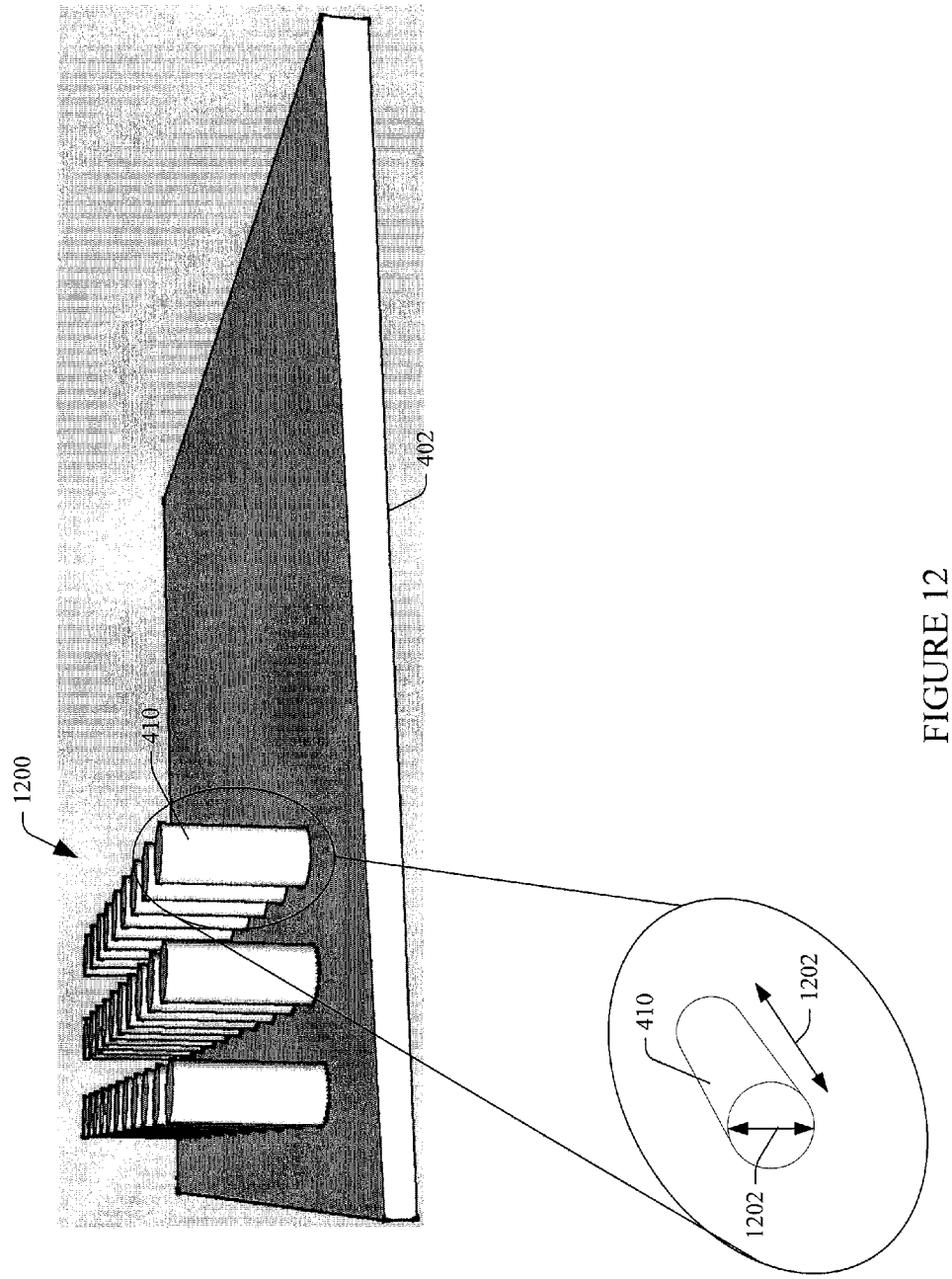
FIG. 12 schematically illustrates an example of a sub-set of the individual x-ray attenuating attenuators in connection with a substrate.

The beam shaper 314 further includes a two dimensional array of individual x-ray attenuating elements or attenuators 410 (shown as black dots in FIG. 4). The attenuators 410 include a high Z material such as tungsten, tantalum, gold, platinum, and/or other high Z material. As such, the attenuators 410 fully or substantially fully attenuate x-rays incident thereon. An example of a sub-set 1200 of the individual x-ray attenuating attenuators 410 is shown in connection with the substrate 402 in FIG. 12. In FIG. 12, the x-ray attenuating attenuators 410 are cylindrically shaped rods, wires, bars or the like, having a length 1202 in a range from three hundred (300) to one thousand (1000) microns and a diameter 1204 in a range from ten (10) to sixty (60) microns. In another embodiment, the individual x-ray attenuating attenuators 410 can be cone, rectangular, or otherwise shaped.

Figure 5:
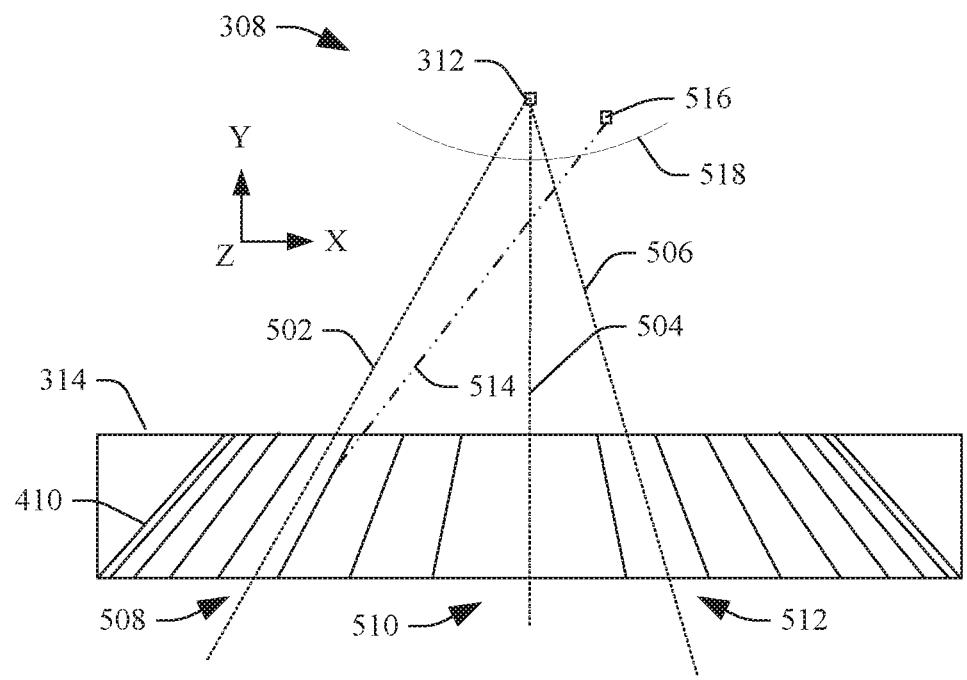
FIG. 5 schematically illustrates the beam shaper with attenuators focused at a focal spot.

In FIG. 12, the illustrated attenuators 410 of the substrate 402 are individually focused towards the focal spot 312, which may facilitate reducing off-focal rays, dose, off focal corrections, etc. by filtering off focal rays. By way of further example, FIG. 5 schematically illustrates a side view of the beam shaper 314 looking in the z-axis direction, showing attenuators 410 focused at the focal spot 312, where on-focal rays 502, 504, and 506 emitted from the focal spot 312 respectively pass through interstices 508, 510, and 512 between attenuators 410, and an off focal ray 514 emitted from another region 516 of an anode 518 of the source 308 is attenuated by an attenuator 410. In another embodiment, the attenuators 410 are not focused at the focal spot 312.

Figure 6:
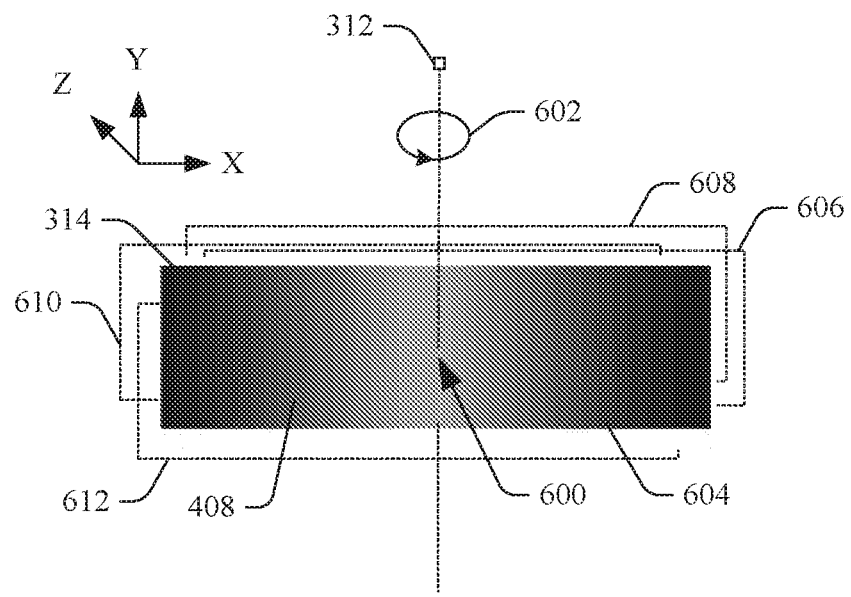
FIG. 6 schematically illustrates example physical movement of the beam shaper to blur any shadow caused by the radiation attenuating elements of the beam shaper.

Returning to FIG. 4, in the illustrated embodiment, the attenuators 410 are small enough (e.g., 10-30 microns in diameter) such that they do not cause a disruptive shadow to cast on the detector array 322. However, where the attenuators 410 cause such a shadow, the substrate 402 can be moved during scanning to blur out the shadow. A non-limiting approach is shown in connection with FIG. 6, which shows a top down view, looking into the beam shaper 314 in a direction from the focal spot 312 to the examination region in the y direction. In FIG. 6, the density of the attenuators 410 is represented in gray scale, where darker gray regions represent a greater density of attenuators 410 and lighter gray regions represent less dense regions of attenuators 410.

In the approach of FIG. 6, a center region 600 of the beam shaper 314 is moved through a predefined orbit 602 in the z-x plane, for example, from position 604, to position 606, to position 608, to position 610, to position 612, and back to position 604, one or more times as a scan is being performed. It is to be understood that the illustrated movement is not limiting. For example, other orbits are contemplated herein. In addition, there may be more or fewer positions. Moreover, positions for subsequent orbits may or may not overlap. To move the beam shaper 314, in one non-limiting instance, the beam shaper can be mounted on or affixed to a moveable support, which is moved via a motor controlled by a motor controller. Other approaches, including, but not limited to, those that would occur to one of ordinary skill in the art, are also contemplated herein.

Returning to FIG. 4, the attenuators 410 are embedded in the low Z material, which can be a solid or semi-so lid such as a gel. In another embodiment, the attenuators 410 can be part of the substrate 402. The illustrated attenuators 410 are arranged in a pattern such that a density of the attenuators 410 nearer a central region 412 of the substrate 402 is lower than a density of attenuators 410 farther away from the central region 412 such as in regions 414 and 416, and the attenuators 410 are separated or spaced apart in the substrate 402 from each other. In this example, the density linearly varies. In other embodiments, the density can vary in a non-linear manner. In FIG. 4, the density of attenuators 410 is represented by the distance between the dots, with a cluster of more dots indicating a higher density.

The illustrated pattern of attenuators 410 is deterministic and symmetric about the center region 412. In this example, the radial spatial gradient of x-ray absorption ranges from approximately zero in the central region 412 of the scanner to approximately 70% at the edge of the beam in regions 414 and 416. In other embodiments, the pattern may be random and/or non-symmetric. The attenuators 410 may have the same diameter or at least two of the attenuators 410 may have different diameters. The shape and/or length of the attenuators 410 can be the same or two or more of the attenuators 410 can have different shapes and/or lengths.

Figure 7:
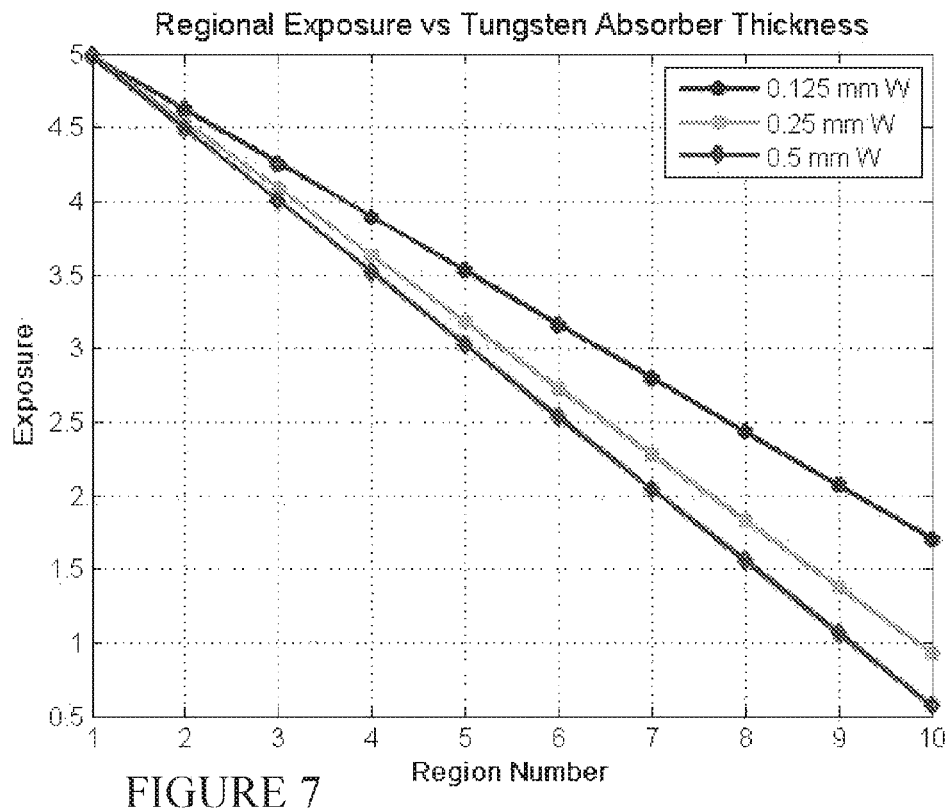
FIG. 7 illustrates how thickness of the attenuating elements determines the transmission of the beam shaper.

The thickness of the attenuators 410 determines the transmission of the beam shaper 314. This is illustrated in FIG. 7, where the y-axis represents exposure or transmission and the x-axis represents regions of attenuators 410. Higher region numbers correspond to a greater density of attenuators 410. FIG. 7 shows three example curves of x-ray transmission as a function of region number (density of tungsten attenuators 410) for three different tungsten attenuator thicknesses. The three curves show that the higher the density of tungsten attenuators 410, the greater the reduction of the number of rays exiting the beam shaper 314 and hence the lower the exposure.

Figure 8:
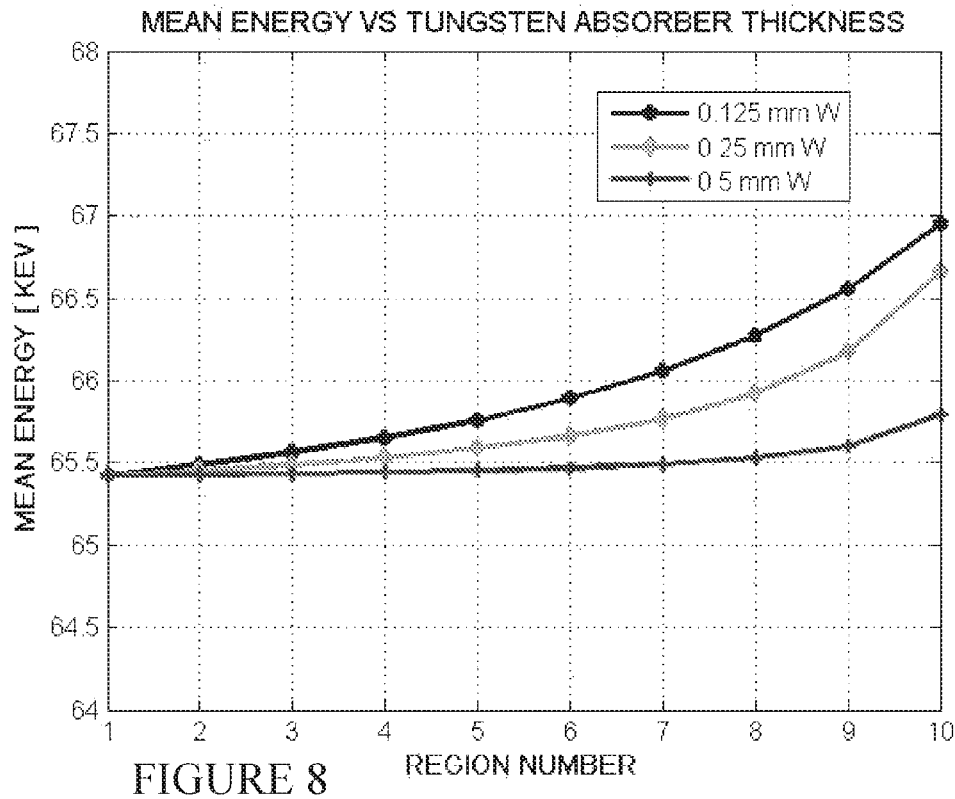
FIG. 8 illustrates the spectrum of x-rays passing through the beam shaper.

FIG. 8 illustrates the spectrum of x-rays passing through the beam shaper 314. The y-axis represents mean energy and the x-axis represents density of attenuators 410 in terms of region number where higher regions number corresponds to a greater density of attenuators 410. FIG. 8 shows three example curves of mean energy as a function of region number (density of attenuators 410) for the three different tungsten attenuator thicknesses.

Various technologies can be used to manufacture the beam shaper 314, including, but not limited to, laser sintering, photo-lithography, advanced printing technology, etc.

Variations are contemplated.

Figure 9:
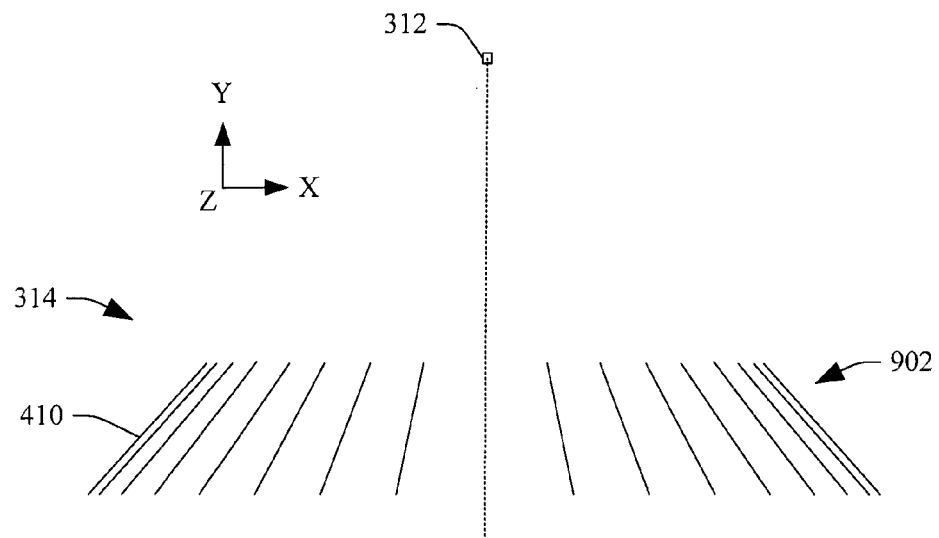
FIG. 9 schematically illustrates a beam shaper including a plurality of septa, each including a plurality of attenuators.

In FIG. 4, the beam shaper 314 includes a generally radiation transparent substrate 402 with a plurality of radiation attenuators 410 embedded therein. FIG. 9 illustrates a variation in which the beam shaper 314 includes a plurality of columns 902 of septa (each extending along the z-axis direction and each having a plurality of radiation attenuators 410 separated from each other) arranged along the x-axis direction, thereby forming a two dimensional beam shaper. The columns 902 can be held in place by a support or otherwise.

Continuing with FIG. 9, in an analogous variation, the beam shaper 314 can include a plurality of rows of septa (each extending along the x-axis direction and each having a plurality of radiation attenuators 410 separated from each other) arranged along the z-axis direction, thereby forming a two dimensional beam shaper.

Figure 10:
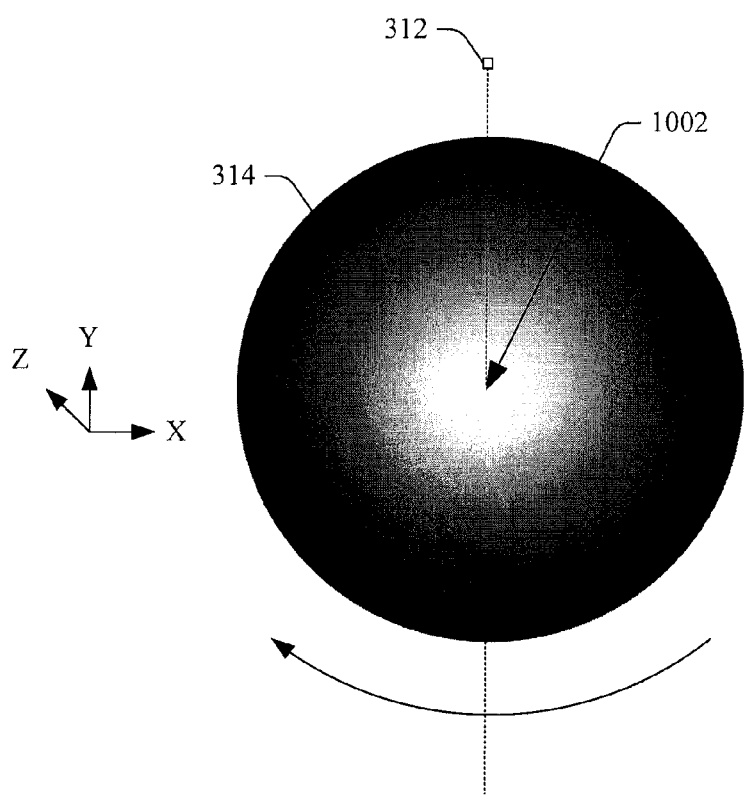
FIG. 10 schematically illustrates a beam shaper configured to shape the transmission profile in the x-z plane.

With the beam shaper 314 illustrated in FIG. 4, the density of the attenuators 410 varies along the x-direction. A variation, in which the beam shaper 314 varies in multiple dimensions in the x-z plane, is shown in FIG. 10, which shows a top down view, looking into the beam shaper 314 in a direction from the focal spot 312 to the examination region in the y direction. With this variation, the beam shaper 314 is circular shaped, and the density of attenuators 410 increases from a central region 1002 with radial symmetry. In this example, the beam shaper 314 has a diameter of less then six inches. Larger diameters are also contemplated herein. Likewise, the thickness can be less than a half a millimeter or greater than a half a millimeter. Similar to FIG. 6, the density is represented in gray scale with darker shades of gray having greater density of the attenuators 410 and lighter shades of gray having less density of the attenuators 410. Likewise, the pattern may or may not be deterministic and/or symmetric.

Continuing with FIG. 10, the density of the attenuators 410 in the z-axis direction can also be varied to facilitate intensity-compensating for the "heel" effect of rays that leave the anode. With the "heel" effect, the intensity of the beam on the side of beam closer to the anode and farther from the cathode generally is lower than the intensity of the beam on the side of beam closer to the cathode and farther from the anode. In one embodiment, the density of the attenuators 410 in the z-axis direction can be varied so that the intensity is more uniform across the beam. For example, the density can be greater farther away from the anode to decrease the intensity so that the intensity of the beam on the side of beam closer to the cathode is closer to the intensity of the beam on the cathode side of the beam.

Continuing with FIG. 10, approaches for mitigating blur include an approach similar to that discussed in FIG. 6 where the beam shaper 314 moves through the orbit 602, an approach in which the beam shaper 314 rotates such as in the x-z plane about the center region 1002 (as show in FIG. 10), and/or otherwise.

In the illustrated embodiments, shadow is mitigated by moving the beam shaper 314. Additionally or alternatively, shadow can be mitigated by dithering the focal spot 312 to cause blurring of the projections. Focal spot motion can be controlled by electro-static deflection, magnetic deflection and/or otherwise. The focal spot may also dithered by intentionally shaping the anode such that the focal spot moves slightly as the anode rotates (e.g., target wobble).

Figure 11:
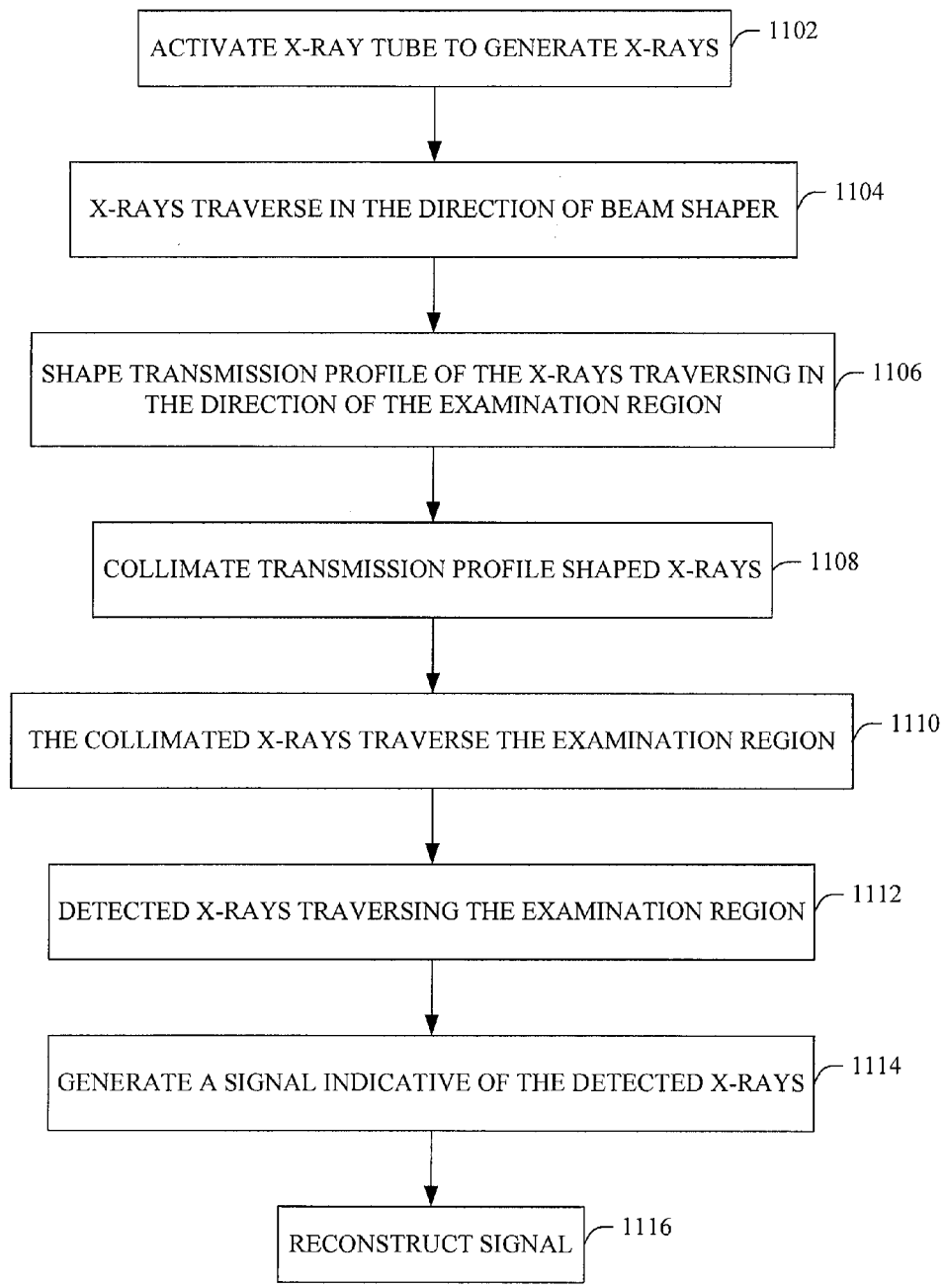
FIG. 11 illustrates an example method.

FIG. 11 illustrates example operation of the system 300.

It is to be appreciated that the ordering of the below acts is for explanatory purposes and not limiting. As such, other orderings are also contemplated herein. In addition, one or more of the acts may be omitted and/or one or more other acts may be included.

At 1102, an x-ray tube of a scanner is activated to generate x-rays.

At 1104, a sub-portion of the x-rays traverse in a direction of a beam shaper.

At 1106, the beam shaper attenuates the x-rays traversing the beam shaper to a lesser degree near a center region and to a greater degree away from the center region. This can be achieved as described herein using the beam shaper 314, which includes a varying density of the attenuators 410 at least across the x-direction.

At 1108, the beam exiting the beam shaper is collimated.

At 1110, the collimated beam traverses the examination region and a portion of a subject or object therein.

At 1112, the beam traversing the portion of the subject or object therein is detected by a detector array of the scanner.

At 1114, the detector array generates a signal indicative of the detected radiation.

At 1116, the signal is reconstructed, generating volumetric image data indicative of the scanned portion of the subject or object.

The above may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. An imaging system, comprising:
   a radiation source that emits x-ray radiation from a focal spot in a direction of an examination region, and radiation source rotates about the examination region and about a z-axis along which defines a z-direction, with a y-axis defining a y-direction orthogonal to the z-direction, and an x-direction defining an x-axis orthogonal to the z-direction and y-direction;
   a beam shaper located between the focal spot and the examination region, that shapes an x-ray transmission profile of the x-ray radiation emitted from the source and incident on the beam shaper such that the radiation leaving the beam shaper has a pre-determined transmission profile, wherein the beam shaper has a central region along the z-direction and further includes a two dimensional array of individual radiation attenuating elements attenuating x-ray radiation separated from each other, embedded in a substrate and arranged such that a density of the attenuating elements increases from the central region in a direction away from the central region along the x-axis direction, wherein the individual radiation attenuating elements fully or substantially fully attenuate x-rays, wherein the attenuating elements are focused at the focal spot; and
   a source collimator disposed between the beam shaper and the examination region which collimates the shaped x-ray radiation.

2. The imaging system of claim 1, wherein the attenuating elements are arranged such that a density of the attenuating elements increases radially from the central region in a direction away from the central region in the x-direction and the z-direction.

3. The imaging system of claim 1, wherein the attenuating elements attenuate off-focal x-rays.

4. The imaging system of claim 1, wherein a pattern of the attenuating elements in the beam shaper is deterministic.

5. The imaging system of claim 1, wherein a pattern of the attenuating elements in the beam shaper is random.

6. The imaging system of claim 1, wherein the substrate includes a substantially x-ray transparent material, wherein the attenuating elements are non-moveably embedded in the substrate.

7. The imaging system of claim 1, further comprising:
   a plurality of rows or columns of septa, wherein each row or column of septa includes a plurality of the attenuating elements separated from each other, and the septa are arranged separated from each other.

8. The imaging system of claim 1, wherein at least two of the attenuating elements have a different geometry.

9. The imaging system of claim 1, wherein the beam shaper has at least one of:
   a geometry of less than six inches in length by less than six inches in width in the z-direction and x-direction; or
   a geometry of less than six inches in diameter in a plane formed by the z-direction and the x-direction.

10. The imaging system of claim 1, wherein the beam shaper has a thickness in a range of a quarter of a millimeter to ten millimeters in the y-direction.

11. The imaging system of claim 1, further comprising:
    a moveable support, wherein the beam shaper is affixed to the moveable support, which is configured to controllably move during scanning relative to the focal spot, thereby moving the beam shaper during scanning.

12. The imaging system of claim 11, wherein the beam shaper moves along an orbit with an axis fixed relative to the focal spot and the beam shaper remaining in parallel planes in the z-direction and y-direction during scanning or rotates during scanning about an axis in the y-direction.

13. The imaging system of claim 11, wherein moving the beam shaper introduces blur which blurs out shadow cast by the attenuators.

14. An imaging system, comprising:
    a radiation source that emits x-ray radiation from a focal spot in a direction of an examination region, and radiation source rotates about the examination region and about a z-axis along which defines a z-direction, with a y-axis defining a y-direction orthogonal to the z-direction, and an x-direction defining an x-axis orthogonal to the z-direction and y-direction;
    a beam shaper located between the focal spot and the examination region, that shapes an x-ray transmission profile of the x-ray radiation emitted from the source and incident on the beam shaper such that the radiation leaving the beam shaper has a pre-determined transmission profile, wherein the beam shaper has a central region along the z-direction and further includes a two dimensional array of individual radiation attenuating elements attenuating x-ray radiation separated from each other, embedded in a substrate and arranged such that a density of the attenuating elements increases from the central region in a direction away from the central region along the x-axis direction, wherein the individual radiation attenuating elements fully or substantially fully attenuate x-rays, wherein the attenuating elements are focused at the focal spot, wherein the attenuating elements each have a same geometry and vary in length radially according to a distance from the focal spot; and a source collimator disposed between the beam shaper and the examination region which collimates the shaped x-ray radiation.

15. A method, comprising:

shaping a transmission profile of an x-ray beam used to scan a subject or object so that the transmission profile that is a number of emitted x-rays as a function of beam angle decreases from a central region of the x-ray beam directed toward the subject to a periphery of the x-ray beam using a beam shaper that includes a two dimensional array of attenuating elements attenuating x-ray radiation disposed in an x-direction and a z-direction orthogonal to the x-direction and each of the attenuating elements are separated from each other and arranged such that a lesser density of the attenuating elements are located nearer the central region and greater density of the attenuating elements are located farther from the central region, wherein the density decreases along the x-direction and the z-direction; and scanning the subject or object using the x-ray beam with the shaped transmission profile and collimated.

16. The method of claim 15, wherein the attenuating elements include a material that substantially attenuates x-rays incident thereon.

17. The method of claim 15, further comprising:

moving the beam shaper through an orbit in a plane while scanning the subject or object.

18. A beam shaper configured for use in an imaging system, comprising:

a two dimensional array of individual x-ray radiation attenuating elements disposed in a plane with an x-axis and a z-axis, separated from each other and arranged fixed with respect to each other such that a density of the attenuating elements varies along the x-axis direction, wherein the individual radiation attenuating elements fully or substantially fully attenuate x-rays; and wherein the x-ray radiation attenuating elements are one of cone or bar shaped.

19. The beam shaper of claim 18, wherein the individual x-ray radiation attenuating elements are separated from each other and arranged with respect to each other such that a density of the attenuating elements varies along a z-axis direction.

20. The beam shaper of claim 18, further comprising:

a substrate including a substantially x-ray transparent material, wherein the x-ray radiation attenuating elements are non-moveably embedded in the substrate.

21. A beam shaper configured for use in an imaging system, comprising:

a two dimensional array of individual x-ray radiation attenuating elements disposed in a plane with an x-axis and a z-axis, separated from each other and arranged fixed with respect to each other such that a density of the attenuating elements varies along the x-axis direction, wherein the individual radiation attenuating elements fully or substantially fully attenuate x-rays; and a plurality of rows or columns of septa, wherein each row or column of septa includes a plurality of the x-ray radiation attenuating elements separated from each other, and the septa are arranged separated from each other.

* * * * *